United States Patent [19]

Jarvis, Jr. et al.

[11] Patent Number: 4,680,174

[45] Date of Patent: Jul. 14, 1987

[54] INDUCTION OF IMMUNE RESPONSE BY IMMUNIZATION WITH ENCAPSULATED ANTIGEN-PRODUCING CELLS

[75] Inventors: Allan P. Jarvis, Jr., Newburyport; George A. Koch, Medfield, both of Mass.; Paul G. Abrams, Washington, D.C.

[73] Assignee: Damon Biotech, Inc., Needham Heights, Mass.

[21] Appl. No.: 613,803

[22] Filed: May 24, 1984

[51] Int. Cl.$^4$ .................. A61K 39/395; C12N 15/00; C12P 21/00

[52] U.S. Cl. ........................................ 424/85; 435/68; 435/172.2; 935/89; 935/107

[58] Field of Search .............. 424/85, 88; 435/68, 435/172.2, 240; 935/89, 107

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,409,331 | 10/1983 | Lim | 435/178 |

OTHER PUBLICATIONS

Brown, Dilley, Levy, Journal of Immunology, vol. 125, No. 3, Sep. 1980, Immunoglobulin Secretion by Mouse X Human Hybridomas: An Approach for the Production of Antiidiotype Reagents Useful in Monitoring Patients with B Cell Lymphoma.

Hatzubai, Maloney, Levy, The Journal of Immunology, vol. 126, No. 6, Jun. 1981, The Use of a Monoclonal Anti-Idiotype Antibody to Study the Biology of a Human B Cell Lymphoma.

Miller et al, New England Journal of Medicine, vol. 306, No. 9, Mar. 4, 1982, Treatment of B-Cell Lymphoma with Monoclonal Anti-Idiotype Antibody.

*Primary Examiner*—Blondel Hazel
*Attorney, Agent, or Firm*—Lahive & Cockfield

[57] ABSTRACT

Cells such as genetically modified cells, e.g., hybridoma, which secrete an antigenic substance are encapsulated within capsule membranes having pores of dimensions sufficient to permit efflux of the antigens secreted by the cells but insufficient to permit traverse of the cells. The capsules are injected into an experimental animal where antigen passing through the pores of the capsule membrane induces lymphocytes to produce antibodies complementary to the antigen. The antibody may be harvested from the circulatory system of the animal. Preferably, lymphocytes are sampled from, e.g., the spleen of the animal, fused with a malignant cell line to produce a hybridoma which synthesizes the antibody in vivo, and the hybridoma is cultured to produce large quantities of monoclonal antibody.

30 Claims, 1 Drawing Figure

|   | 1 | | 2 | | 3 | |
|---|---|---|---|---|---|---|
|   | – | – | 3 | 2 | 1 | 2 |
| A | BLANK | | .471 | | .653 | |
|   | – | – | 3 | 2 | 1 | 2 |
| B | .088 | | .463 | | .699 | |
|   | – | – | * | * | 3 | 6 |
| C | .004 | | .168 | | .316 | |
|   | – | – | * | * | 3 | 6 |
| D | .020 | | .184 | | .280 | |
|   | 2 | 2 | 1 | 3 | 2 | 3 |
| E | .788 | | .606 | | .937 | |
|   | 2 | 2 | 1 | 3 | 2 | 3 |
| F | .894 | | .559 | | .800 | |
|   | 1 | 6 | 2 | 6 | 3 | 3 |
| G | .555 | | .540 | | .299 | |
|   | 1 | 6 | 2 | 6 | 3 | 3 |
| H | .504 | | .572 | | .270 | |

*FIG. 1*

INDUCTION OF IMMUNE RESPONSE BY IMMUNIZATION WITH ENCAPSULATED ANTIGEN-PRODUCING CELLS

BACKGROUND OF THE INVENTION

This invention relates to the production of antibodies. More particularly, it relates to a method of inducing an immune response in an experimental animal by introducing into the animal cells which produce and secrete an antigen.

Antibodies are now widely used in the purification of biological materials and in diagnostic testing and have recently been used therapeutically to treat certain types of lymphomas and melanomas. The production of antibodies against a specific antigen has been approached in the prior art by injection of the antigen into an experimental animal, typically two or more times, and then harvesting antibody from serum. More recently, with the advent of hybridoma technology, rather than collecting antibody from the animal's circulatory system, a sample of lymphocytes is taken from the animal, typically from the spleen, and the cell sample is fused with an immortal cell line such as a myeloma. The fusion products are screened to detect viable hybridomas which secrete the antibody. These hybridomas are then cultured to produce colonies from which relatively large quantities of monoclonal antibody may be harvested.

One important factor in the foregoing procedure is the degree of purity of the antigen used to induce the immune response. Where one seeks antibody complementary to a specific biological material produced by cells, concentration and purification of the particular antigen from the wide variety of proteins, glycolipids, glycoproteins, lipoproteins, and polysaccharides that are typically present in the secretions is often both tedious and a key factor in successful production of the antibody of interest. To the extent the sample of antigen used for immunization contains extraneous materials, the immunized animal produces a large number of antibodies of differing specificity, only a small portion of which constitute the antibody of interest. Consequently, purification of the antibody from the antisera is tedious. Furthermore, if one seeks a lymphocyte which is producing the antibody of interest, it is necessary to employ elaborate screening procedures to detect the subset of cells of interest. Additionally, purification of the antibody of interest from bleedings or isolation of a subset of lymphocytes producing the antibody of interest is simplified if the immunizing agent comprises a relatively pure antigen sample.

In the production of antibody to a non-secreted material, e.g., a cell surface antigen (immunoglobulin), or antibody intended for purification of substances produced by cells, e.g., interferons, it is now within the skill of the art to produce a genetically modified cell line which secretes the surface antigen or larger amounts of the interferon. Purification of the cell secretions to concentrate the material of interest and to remove at least some extraneous material is nevertheless desirable or mandatory.

Recently, as reported, for example, by Hatzubai et al. (Journal of Immunology, Vol. 126, No. 6, June, 1981), and Miller et al. (New England Journal of Medicine, Mar. 4, 1982, page 517), a promising method for treating certain types of lymphoma has been developed. The technique is based on the observation that tumors result from the uncontrolled proliferation of clones of (B) cells that express on their surfaces markers restricted to an immunglobulin molecule, including, in part, a structure characteristic of the lymphoma clone. The distinguishing immunoglobulin region (idiotype) of each lymphoma clone is substantially unique and can distinguish tumor cells from normal cells in the patient. The tumor cells do not secrete the idiotype-bearing immunoglobulin molecule, but its secretion can be induced by fusing the lymphoma cell with a myeloma cell line. The resulting fusion products (hybridomas) are screened for secretion of the idiotype-bearing immunoglobulin. A simplified screening procedure is disclosed in co-pending application Ser. No. 613,235, the disclosure of which is incorporated herein by reference.

After culturing and harvesting of a crude product, the idiotype is purified by various chromatography techniques and experimental animals are injected with a small dose of the monoclonal idiotype product followed by a booster injection at 3–4 weeks later. A few days thereafter, the animal's spleen is removed and spleen cells are fused with, e.g., a myeloma cell line. After screening and cloning, anti-idiotype antibody is collected and purified in quantities sufficient for therapeutic use. Intravascular injection of about 150 mg of antibody has been associated with extended remission.

The requirement for antibody tailored to each patient puts serious constraints on this cancer treatment approach. As noted in Miller et al.'s paper (referenced above), more streamlined procedures for producting these anti-idiotype antibodies would be likely to facilitate using anti-idiotype antibodies in this clinical treatment.

SUMMARY OF THE INVENTION

In accordance with the instant invention, it has been discovered that an immune response in an animal body to an antigenic material secreted by a cell can be efficiently induced by implanting directly into the animal body living cells encased in one or more capsule membranes. The membranes comprise pores of dimensions sufficient to permit passage of the antigenic material but to preclude passage of the encapsulated cells. Surprisingly, it has been found that an antigen secreted by cells, e.g., IgG having a molecular weight of 150,000 daltons, or IgM that may be as large as 950,000 daltons can traverse the capsule membranes and induce the appropriate immune response in the animal, yet the animal's immune system does not destroy the cells. Furthermore, the encapsulated, antigen-secreting cells undergo normal metabolism including mitosis provided they are supplied with appropriate nutrients in the culture prior to encapsulation, after encapsulation and before implantation, or after implantation. While any cell which secretes an antigen for which a complementary antibody is desired may be used in the process, in preferred embodiments of the invention a genetically modified prokaryotic or eukaryotic cell designed specifically to secrete relatively large quantities of the antigen is employed.

Practice of the invention facilitates production of antibody because the often tedious step of purifying the antigen in preparation for immunization is not required. Rather than purifying the antigen of interest from the mixture of immunoglobulins and other materials secreted by the cell, one simply encapsulates the cell or a plurality of the cells and employs the capsules as the immunizing agent. Typically, no booster injection is required. Also, the capsule membranes may be engineered to have a selected permeability range such that much extraneous high molecular weight antigenic material remains within the implanted microcapsule and does not induce extraneous immune responses. Thus, for example, IgGs may be dispensed in vivo while IgMs are retained, or pyrogens may be retained while lower molecular weight antigen is released.

After immunization, the antibody of interest may be harvested directly from bleedings taken from the experimental animal. Alternatively, a lymphocyte from, e.g., the spleen, may be sampled, fused with a malignant cell such as a myeloma cell, and cloned to produce a culture from which relatively large quantities of monoclonal antibody can be obtained.

It is an object of the invention to provide a method of inducing an immune response in an animal to a selected antigen which does not require purification of the antigen. Another object is to immunize with living cells while avoiding immune rejection of the cells. Another object is to provide a more streamlined method of producing monoclonal antibodies. Another object is to induce an immune response in an animal body using an immunizing vehicle which dispenses antigen more or less continuously over a period of time and thus normally requires no booster injection. These and other objects and features of the invention will be apparent from the following description, from the drawing, and from the claims.

BRIEF DESCRIPTION OF THE DRAWING

The sole FIGURE of the drawing is a chart indicating the results of an experiment demonstrating the production of anti-anti-Azotobacter nitrogenase in laboratory animals immunized with encapsulated hybridoma which secretes anti-Azotobacter nitrogenase.

DESCRIPTION

The broad concept of the invention is to induce an immune response in an experimental animal to an antigenic substance secreted by a living cell so as to produce antibodies complementary to the antigen while avoiding the tedious steps of collecting and purifying the antigenic substance from the cells. The invention is essentially unlimited as to the type of cell or antigen employed provided the cell secretes the antigen and the antigen has a molecular weight of less than about $10^6$ daltons. Eukaryotic or prokaryotic cells may be used. Genetically modified cells designed specifically to secrete relative large amounts of the antigen of interest are preferred.

Thus, where it is desired to produce antibody specific to a substance secreted at low concentration by a cell, now conventional genetic engineering techniques may be employed to produce a cell line which secretes the antigen in greater concentrations. Gene insertion or hybridoma technology may be employed. Exemplary techniques are disclosed in U.S. Pat. No. 4,232,224, issued Dec. 2, 1980, for gene insertion, and Koprowski et al., "Production of antibodies against influenza virus by somatic cell hybrids between mouse myeloma and primed spleen cells," Proc. Nat. Acad. Sci. USA 74: 2985 (1977), for hybridoma formation. For example, where it is desired to produce antibody specific to an interferon, e.g., for purposes of purification of the interferon, the DNA fragment which codes for interferon production may be inserted by use of a suitable vector into a prokaryotic cell host, e.g., E.coli, which is cloned to produce a culture which secretes the interferon.

Where it is desired to produce antibody complementary to an antigenic substance which is not secreted by a cell, e.g., cell membrane bound antigens (immunoglobulins), the cell may be fused with a malignant cell line, e.g., a myeloma, to produce a hybridoma which secretes the antigen of interest.

When the cell of interest has been selected, it may be cultured either before or after microencapsulation to produce a cell colony by mitosis which secretes a sufficient amount of the antigenic substance to induce a good immune response. Generally, the number of cells required depends upon the amount of secreted antigen that the cell line produces and on the type of experimental animal within which the encapsulated cells are to be implanted.

The cells may be encapsulated generally in accordance with the process disclosed in U.S. Pat. No. 4,352,883 to Franklin Lim, issued Oct. 5, 1982, the disclosure of which is incorporated herein by reference. In accordance with the Lim technique, a prokaryotic or eukaryotic cell or cell culture, including genetically modified cells and tissue, may be encapsulated without substantial damage. The cells after encapulation are healthy, viable, capable of ongoing normal metabolism, secrete the materials they normally secrete while disposed within the capsules, and can undergo mitosis. Recent experiments have indicated, in accordance with the broad disclosure of the patent, that it is possible to control the dimensions of the pores of the capsule membranes such that immunoglobulins secreted by cells, which have a molecular weight greater than about 100,000 daltons, traverse the membranes. It has now been discovered that such relatively high molecular weight materials, when produced by encapsulated cells implanted in an animal body, can traverse the cell membrane and induce an immune response. However, the cells secreting the antigen are protected from immunological rejection and thus remain viable for extended periods to serve as a continuing source of the antigenic substance. Although a second injection of encapsulated cells or unencapsulated antigen may be conducted if desired, normally no booster shot is required to reinforce the immune response.

Furthermore, the dimensions of the microcapsule pores may be controlled as disclosed herein and in the Lim patent to preferentially permit traverse of substances having a relatively low molecular weight while retaining all or at least a portion of higher molecular weight substances. Thus, during encapsulation a degree of control may be exercised over the molecular weight of the substances that are released into the animal body. For example, genetically engineered prokaryotic cells which secrete both (1) an antigen of interest having a molecular weight below, e.g., about 70,000 daltons and (2) pyrogens having a greater molecular weight and thus greater effective molecular dimensions may be encapsulated such that a substantial fraction of the pyrogens are retained within the capsules while an immune response is developed against the lower molecular weight antigenic substance of interest. As another example, in accordance with the teachings disclosed herein, it is possible to encapsulate cells which secrete both IgG and IgM such that the IgG is dispensed into the animal body while all or most of the IgM is retained within the intracapsular volume. Accordingly, practice of the invention effectively provides a degree of "purification" of the antigen of interest in that antigen is delivered to the animal body less diluted by higher molecular weight substances. The purification of the antigen is achieved without denaturation, a common problem in conventional techniques.

The capsules are preferably implanted, conveniently by injection, for example, in the peritoneal cavity of a laboratory animal such as a rat, mouse, or other mammal. Intramuscular or subcutaneous implantation may also be used.

The presently preferred method of encapsulating the cells, as noted above, is disclosed in U.S. Pat. No. 4,352,883. The tissue sample, cell, or cell culture to be encapsulated is first prepared in finely divided form in accordance with well-known techniques and suspended in an aqueous medium suitable for maintenance and for supporting the ongoing metabolic processes of the particular cells involved. Media suitable for this purpose generally are available commercially. Thereafter, a water-soluble substance which is physiologically compatible with the cells and which can be rendered water-insoluble to form a shape-retaining coherent spheroidal mass or other shape is added to the medium. The solution is then formed into droplets containing cells together with their maintenance or growth medium and is immediately rendered water-insoluble and gelled to form shape-retaining, typically spheroidal coherent masses. The material used to induce gelation of the culture medium may be any non-toxic water-soluble material which, by a change in the surrounding temperature, pH, ionic environment, or concentration, can be converted to shape-retaining masses. Preferably, the material also is one which comprises plural, easily ionized groups, e.g., carboxyl or amino groups, which can react by salt formation with polymers containing plural groups which ionize to form species of the opposite charge. Use of this type of material enables the deposition of a membrane of a selected porosity range without damage to the labile cells.

The presently preferred materials for forming the gelled masses are water-soluble natural or synthetic polysaccharides. Many such commercially available materials are typically extracted from vegetable matter and are often used as additives in various foods. Sodium alginate is the presently preferred water-soluble polysaccharide. Other usable materials include acidic fractions of guar gum, gum arabic, carrageenan, pectin, tragacanth gum or xanthan gums. These materials may be gelled when multivalent ions are exchanged for the acidic hydrogen or alkali metal ion normally associated with the carboxyl groups. The liquid, water-soluble polysaccharide molecules are thus "cross-linked" to form a water-insoluble, shape-retaining gel which often can be resolubilized on removal of the cross-linking ions, by ion exchange, or via a sequestering agent. Preferably, physiologically compatible ions, e.g., calcium, are employed because their use tends to have little adverse impact on the viability and normal metabolism of cells. Other polysaccharides can be switched between the water-soluble state and the gelled, water-insoluble state simply by changing the pH of the medium in which they are dissolved.

A typical cell culture medium - polysaccharide solution composition comprises equal volumes of cells in their medium and a 1-2% solution of polysaccharide in physiological saline. When employing the preferred sodium alginate, a 1.0-1.5% solution has been used with success.

In the next step of the process, the polysaccharide solution containing the cells is formed into droplets of a convenient size, generally within the range of 50 microns to a few millimeters. Thereafter, the droplets are immediately immersed in a calcium salt bath to cross-link the gel to form the shape-retaining, high viscosity spheriodial masses containing the suspended cell or cells and its medium. The gelled spheres collect in the solution as a separate phase and may be separated by aspiration.

Next, a semipermeable membrane is deposited about the surface of the gel spheres. The preferred method of forming the membrane is to permanently cross-link surface layers of the spheres or other gelled shapes by subjecting them to an aqueous solution of a polymer, generally having a molecular weight greater than about 3,000 daltons, containing groups ionically reactive with functionalities in the gel molecules. When carboxylated or other acidic polysaccharides are used, polymers containing acid reactive groups such as amines, imines, or amides are useful for this purpose. Polycationic materials such as polylysine, polyethyleneimine, polyornithine, and polyvinylamine are presently preferred for this step. Exposure to the polycationic materials results in the formation of salt bond-type cross-links by interaction between the anionic groups, e.g., carboxyl groups, on the polysaccharide, and the cationic groups, e.g., amine groups, on the polymer.

Depending on the type of semipermeable membrane formation technique employed, it is often desirable to treat the capsules so as to occupy free amino groups or the like which might otherwise impart to the capsule a tendency to clump. This can be done, for example, by immersing the capsule in a solution of sodium alginate.

In accordance with the Lim encapsulation technique, the permeability of the membrane can be controlled in part by selecting the molecular weight of the cross-linking polymer used, the duration of the cross-linking steps, and the concentration of polymer in the cross-linking solution. For example, a solution of polymer having a low molecular weight, in a given time, will penetrate further into the gel than a high molecular weight polymer. In general, the higher the molecular weight and the less the penetration of the polymer, the larger the pore size of the resulting membrane. As noted above, polymers having a molecular weight greater than about 3,000 daltons are preferred. One set of reaction conditions disclosed in the Lim patent noted above employs polylysine of average molecular weight of about 35,000 daltons dissolved at a concentration of 0.016 weight percent polylysine in saline.

It has been determined that the capsule membranes of the type produced with the foregoing technique comprised pores of dimensions which vary and do not absolutely prohibit molecules of a given effective diameter from traversing the membrane while permitting traverse of smaller molecules. Rather, the pores are believed to comprise tortuous paths through the membrane defined by interstices among the cross-linked polyanionic and polycationic materials used to form the membrane. Thus, for a given set of reaction conditions and a given pair of polycationic materials and polyanionic materials (or mixtures of such materials), low molecular weight substances diffuse freely through the membrane at a relatively rapid rate substantially unhindered by collisions with the membrane material. Molecules having a larger molecular weight and larger effective molecular dimension diffuse through the membrane at a rate which is influenced by the lateral dimensions and length of the pores. Within this higher range of molecular dimensions, as the molecular dimensions increase, the rate of passage through the membrane decreases. The upper limit of the permeability range is difficult to define precisely, but there exists for each system a molecular dimension where the diffusion rate is substantially zero.

Capsules designed for use in the instant invention preferably have membranes tailored to exploit the foregoing semipermeability properties. Thus, during the encapsulation, a degree of control may be exercised over the permeability of the capsule membrane so as to permit diffusion of the antigenic substance of interest while prohibiting passage through the membrane of at least the cell and preferrably extraneous substances present in the culture medium or secreted by the cells which are disposed within the intracapsular volume.

In addition to the permeability control techniques disclosed in the Lim patent, two other porosity control techniques have been discovered.

In a first technique, particularly useful in situations where it is desired to retain molecules having a molecular weight above about 20,000–100,000 daltons within the intracapsular volume while releasing lower molecular weight material, consecutive membrane formation steps may be employed. For example, the gel masses may first be immersed in a solution of high molecular weight polylysine and subsequently in a solution with low molecular weight polylysine. Alternatively, the first membrane formation may involve an intermediate weight polylysine followed by a polycationic polymer having a higher charge density such as polyvinylamine. The effect of this technique is to reduce the average dimensions of the pores.

The second pore dimension control technique has been developed based on the observation that alginate gels vary in volume depending on their degree of hydration, which in turn is dependent upon the ionic strength of the solution with which they are equilibrated. A membrane formed about an expended alginate gel is more uniform than membranes about unexpanded gels. This phenomenon, coupled with the observation that membranes formed about dense gels remain intact when the gel is subsequentially expanded, permits the synthesis of membranes having increased lateral pore dimensions and forming improved membranes. Thus, for example, where the antigen of interest has a molecular weight on the order of 200,000 daltons, the cells which secrete the antigen may be encapsulated, for example, by reacting a moderate molecular-weight polycationic material with high density calcium alginate gel masses containing cells. The capsules may be equilibrated and expanded with a solution of monovalent cations to increase the degree of hydration of the gel, thereby expanding the capsule membranes, and increasing the effective pore size. Optionally, the expanded capsules may again be treated with a cross-linking polymer prior to implantation. Further particulars on controlling the dimensions of membrane pores are disclosed in co-pending application Ser. No. 579,494, the disclosure of which is incorporated herein by reference.

By employing one or a combination of the foregoing techniques, it is possible to empirically set the permeability properties of the membranes to fine tune their inherent sieving capabilities.

Induction of the immune response involves stimulation of lymphocytes by the antigen in the circulatory system of the experimental animal. Harvesting of the antibody may be conducted in accordance with the invention by simply permitting the lymphocytes responsible for synthesis and secretion of the antibody of interest to mature and then collecting and purifying antibody from periodic bleedings using techniques well-known to those skilled in the art. While this conventional antibody harvesting technique is sufficient for small scale antibody production, a preferred harvesting technique involves the now conventional manipulative techniques for producing monoclonal antibodies. In this case, after induction of the immune response, the animal is sacrificed and lymphocytes, typically sampled from the spleen, lumph nodes, or bone marrow, are fused with a immortal cell line such as a myeloma. Preferably, an established malignant cell line which secretes little or no immunuglobulin is employed. Fusion products are screened for viable hybridomas which secrete the antibody, and the hybridomas are then cloned to produce hybridoma cultures which secrete relatively large amounts of monoclonal antibody. Production of hybridomas is preferred where large quantities of antibody specific to a particular antigen are desired, for example, in immunoaffinity chromotography columns, production of diagnostic test kits such as radioimmunoassay and enzyme immunoassay kits, and for therapeutic use, such as the treatment of lymphoma in the manner set forth above. Methods of producing hybridomas are disclosed, for example, in the following articles which are incorporated by reference herein. Koprowski et al, supra; Howard et al, "Isolation of six monoclonal alloantibodies against histocompability antigens: clonal competition," Immunology 41:131(1980); and Trowbridge, "Interspecies spleenmyeloma hybrids producing monoclonal antibodies against mouse lymphocyte surface glycoprotein T200," J. Exptl. Med. 148: 313(1978). A new in vivo method of growing hybridoma colonies is disclosed in co-pending application Ser. No. 579,460, the disclosure of which is incorporated herein by reference.

The invention will be understood further from the following non-limiting examples.

EXAMPLE 1

A cell line secreting IgG antibodies against Azotobacter nitrogenase is established by fusion of spleen cells from a BALB/c mouse immunized with Azotobacter nitrogenase and a BALB/c mouse myeloma cell line, GM 3570 (literature designation P3x63Ag8.653). The myeloma cell line, which does not secrete IgG, was purchased from the Human Genetic Mutant Cell Repository. Myeloma and the anti-Azotobacter nitrogenase secreting spleenic lymphocytes were fused using conventional polyethylene glycol techniques as described in the above references. The fusion products were screened for anti-Azotobacter nitrogenase secretion using techniques as discussed in application Ser. No. 613,235 and viable hybridomas were encapsulated using the following technique.

The BALB/c hybridoma (designated C25) was suspended in a 1.34% (w/v) sodium alginate (NaG-Kelco) in saline solution. The viscous suspension was transferred into a 10 cc syringe and mounted onto a jet head droplet-forming apparatus. A jet head apparatus consists of a housing having an upper air intake nozzle and an elongate hollow body friction fitted into a stopper. A syringe, e.g., a 10 cc syringe, equipped with a stepping pump is mounted atop the housing with a needle, e.g., a 0.01 inch I.D. Teflon coated needle, passing through the length of the housing. The interior of the housing is designed such that the tip of the needle is subjected to a constant laminar airflow which acts as an air knife. In use, the syringe full of the solution containing the material to be encapsulated is mounted atop the housing, and the stepping pump is activated to incrementally force drops of the solution to the tip of the needle. Each drop is "cut off" by the air stream and falls approximately 2.5 cm into a gelling solution where it is immediately gelled by absorption of cross-linking ions. The preferred gelling solution is a calcium ion solution, e.g., 1.2% (w/v) calcium chloride. The distance between the tip of the needle and the calcium chloride solution is great enough to allow the sodium alginate/cell solution to assume the most physically favored shape, a sphere. Air within the tube bleeds through an opening in the stopper. The gelled, shape-retaining spheroidal masses or temporary capsules, which preferably are between 50 microns and a few millimeters in diameter, collect in the solution as a separate phase and can be recovered by aspiration.

The gelled spheres were washed three times with 150 mM sodium chloride, then incubated for six minutes at room temperature in a 1.875 mg/ml solution of poly-L-lysine (Sigma Chemical Company, molecular weight 65,000 daltons). After incubation, the capsules were washed in 25 ml of 5 mM CHES buffer (2-n-cyclohexylamino ethane sulfonic acid, pH 7.5, in 0.2% (w/v) calcium chloride and 150 mM sodium chloride)), once in 0.2% (w/v) calcium chloride in 150 mM sodium chloride and once in a 150 mM sodium chloride. The capsules were then post coated by incubating for an additional four minutes at room temperature in 0.06% (w/v) NaG in 150 mM sodium chloride, washed once in 150 mM sodium chloride and incubated for an additional 15 minutes at room temperature in 55 mM sodium citrate in 150 mM sodium chloride. The solution was decanted and replaced with a fresh 55 mM sodium citrate in 150 mM sodium chloride solution. The capsules were incubated at room temperature for six minutes in the second sodium citrate solution and washed twice with 150 mM sodium chloride, washed once with Dulbecco's modified Eagle's medium (high glucose), and then with Dulbecco's modified Eagle's medium (high glucose) containing 20% fetal calf serum (FCS-Dutchland Laboratories) and pennicillin, streptomycin, 1 mM glutamine, and $5\times10^{-5}$ M mercaptoethanol. The capsules formed by this procedure were permeable to IgG (molecular weight about 160,000 daltons) but substantially impermeable to IgM (molecular weight about 900,000 daltons).

The encapsulated cells were grown in a culture flask for several days then dispersed in a 24 well microtiter plate together with growth medium, Dulbeccos modified Eagle's medium (high glucose) with pennicilin, steptomycin, 20% FCS, 1 mM glutamine and $5\times10^{-5}$ M mercaptoethanol at a concentration of 20% by volume capsules and 80% by volume growth medium. Intracapsular and extracapsular media in each of the wells was assayed periodically using the following assay to assess concentration of the secreted anti-Azotobacter nitrogenase.

The wells of a 96 well EIA plate were coated with 100 μl a 10 μg/ml (1 μg) solution of Azotobacter nitrogenase in phosphate buffer saline. After incubation overnight at 4° C., the excess phosphate buffer saline was shaken off and the wells were post-coated with a 1% bovine serum albumin in PBS solution (BSA-PBS). After one hour, the BSA-PBS solution was shaken off. Samples were diluted using the BSA-PBS solution and standards were made by diluting a 1 μg/ml solution of purified C25 anti-nitrogenase with the same buffer. The samples were allowed to incubate for one hour at 37° C. and the wells were then washed three times with PBS. A 1:1000 dilution of goat anti-mouse IgG conjugated with peroxidase in BSA-PBS was added to each well. After a two hour incubation at room temperature, each well was washed five times with PBS. One hundred μl of a 4 mg/ml orthophenylenediamine, 0.2% (v/v) hydrogen peroxide in 55 M sodium citrate, pH 4.5, was added to each well. After 15 minutes, the reaction was stopped by the addition of 100 μl of 4N HCL. The plates were read on a plate reader for color to determine the concentration of anti-nitrogenase.

After 22 days, when the extracapsular antibody concentration was approximately 1.9 μg/ml and the intracapsular antibody concentration was about 1 μg/ml, the capsules were washed in Dulbecco's phosphate buffered saline (Ca/Mg free-DPBS) and a 0.5 ml volume of capsules in DPBS was injected into the peritoneal cavity of each of three C57 BL/6J mice. The 0.5 ml of capsules contained approximately $2.5\times10^{6}$ cells. At the same time, an equal concentration of unencapsulated Balb/c×Babl/c hybridoma was injected into B6J mice.

Tail bleedings from the mice were assayed for anti-anti-Azotobacter nitrogenase at days two, three, and six days after implantation using the following procedure. A 96 well EIA plate was coded by overnight incubation at 4° C. of 100 μl of 10 μg/μl Azotobacter nitrogenase per well. The excess PBS was shaken off and the wells were post-coated for one hour with a solution of 1% BSA in PBS. After the BSA-PBS solution was shaken off, 100 μl of 10 μg/ml purified C25 anti-nitrogenase was added to each well and allowed to incubate at room temperature approximately one hour. The excess C25 was shaken off, the wells were washed three times with PBS, and of 100 μl of the serum samples diluted 1:2 with heparin in BSA-PBS were placed in each well. After one hour incubation at room temperature, the samples were shaken off, each well was washed three times with PBS, and 100 μl of goat anti-mouse IgM (mu specific) conjugated with peroxidase was added to each well. After a one hour incubation at room temperature, each well was washed five times with PBS and 100 μl of 4 mg/ml orthophenylenediamine and 0.02% (v/v) hydrogen peroxide in sodium citrate, pH 4.5, was added to each well. After about 15 minutes, color developed and the reaction was stopped by the addition of 100 μl of 4N HCL. The plate was read on a plate reader and compared with controls to determine the presence of anti-anti-nitrogenase in the serum. No antibody was detected in any of the mice injected with unencapsulated cells. This finding was consistent with the fact that the BALB/c×BALB/c hybridoma and B6J mice have different histoincompatibility alleles.

The results of the assays in the three test mice and various controls for the presence of anti-anti-Azotobacter nitrogenase are indicative of the successful achievement of an immune response induced in the animals by implantation of the microcapsules is set forth in FIG. 1. Each block in the grid of FIG. 1 represents a well in a microtiter plate in which the assays were conducted. The number in the upper left hand corner of each block of the grid indicates the mouse from which the bleeding was obtained, the number in the upper right corner of each block of the grid indicates the day post implantation that the bleedings were sampled, and the third number in each block indicates the optical density reading of the assay for the antibody taken at 495 nm. The greater the optical density reading, the greater the concentration of anti-anti-Azotobacter nitrogenase in the sample. Wells labeled 1a–1d were negative controls containing bleedings having a zero concentration of the antibody. As is evident from a review of FIG. 1, all of these animals developed a strong immune response which appeared to peak 2–3 days post-innoculation.

EXAMPLE 2

A human-human hybridoma secreting human IgM (obtained from the Biological Response Modifiers Program, National Cancer Institute, Bethesda, Md.) was suspended in a concentration of about $10^6$ cells/ml in 20 ml of 1.37% (w/v) sodium alginate (Kelco) and 0.2 $\mu$g/ml Transferrin (Sigma) in 150 mM sodium chloride. The viscous solution was transferred into a 20 cc syringe and then onto a jet head droplet forming apparatus, as previously described. Spherical droplets were gelled by contact with a 1.2% (w/v) calcium chloride solution. The gelled spheres were washed three times with 150 mM sodium chloride and incubated for six minutes at room temperature in a solution containing 0.25 mg/ml DEAE Dextran and 100 mg/ml poly-L-lysine (Sigma, average molecular weight approximately 65,000 daltons). The capsules were washed in 50 ml of CHES buffer and then washed in 50 ml of 0.2% (w/v) calcium chloride in 150 mM sodium chloride. The capsules were incubated for five minutes at room temperature in 25 ml of 0.06% (w/v) polyvinylamine in 150 mM sodium chloride, washed twice in 150 mM sodium chloride, incubated an additional four minutes at room temperature in a 0.06% (w/v) sodium alginate in 150 mM sodium chloride and washed once again with 150 mM sodium chloride. The capsules then were incubated for 16 minutes at room temperature in a 55 mM sodium citrate in 150 mM sodium chloride solution, the solution was decanted and the capsules were incubated an additional six minutes in a fresh sodium citrate solution. The capsules were then washed once with 150 mM sodium chloride, once with Dulbecco's modified Eagle's medium (high glucose), and finally with the growth medium, Dulbecco's modified Eagle's medium (high glucose) containing 20% FCS, pennicillin, and streptomycin. The cells were then cultured at 20% (v/v), capsules 80% growth medium.

The following assay was developed to determine the amount of human IgM secreted by the cells as well as determining the quantity of IgM in the intracapsular volume and the extracapsular medium. The wells of a 96 well microtiter plate were coated by adding 100 $\mu$l of a 1:500 diluted rabbit anti-human (kappa chain) serum (Cappel) in PBS. After incubating the plates overnight at 4° C., the solution was shaken from the wells and the wells were filled with a 1% BSA-PBS solution. After a one hour incubation at room temperature, the wells were emptied by decanting the liquid. Intracapsular samples were prepared by removing an aliquot of the culture, washing the capsules three times in cold (4° C.) PBS and breaking the capsules with a A-clearance homogenizer. The capsule debris and cells were centrifuged into a pellet at 2,000 rpm for 15 minutes and the supernatnant was collected. The extracapsular samples were simply the medium in which the capsules were grown.

Samples were applied in 2-fold dilutions to the post-coated wells and incubated at room temperature for two hours. The wells were washed three times with PBS and 100 $\mu$l of a 1:500 dilution of rabbit anti-human IgM (mu specific) conjugated to peroxidase (Cappel) was added to each well. After an additional two hours at room temperature, the wells were washed five times with PBS and 100 $\mu$l of a 4 mg/ml orthophenylenediamine, 0.02% (v/v) hydrogen peroxide in sodium citrate, pH 4.5, solution was added. After 15 minutes, the reaction was stopped by adding 100 $\mu$l of 4N HCL to each well. The amount of color in the sample was determined on a plate reader and the amount of IgM was determined by comparing the color to standard wells with known amounts of human IgM.

The above assay showed that at least 5% of the IgM synthesized by the cells was in the extracapsular medium and the remainder was retained within the capsules. By modifications of the capsule technique as delineated in co-pending application Ser. No. 579,494, the majority of the IgM could be released into the medium. The cells have been determined to be synthesizing approximately 1 microgram of IgM per $10^6$ cells per day.

Despite the relatively low amounts of IgM released from the capsules, 0.5 ml of capsules were injected (day 14 after encapsulation) intraperitoneally into BALB/c mice. The immune response of the mice was monitored periodically using a conventional ELISA screening procedure familiar to those skilled in the art. After about 12 days, the animals had mounted an appreciable immune response. At this stage, either the serum could be used or the spleens could be removed, as described below, for fusion with immortal cell lines to form hybridomas which produce anti-human IgM.

On day 21, the spleens were removed from the mice and fused with the immortal cell line GM 3569 myeloma (Human Genetic Mutant Cell Repository) following published procedures. In brief, approximately $10^7$ myeloma cells were mixed with the cells from one spleen which had been separated by forcing the spleen through a wire mesh screen. The mixture was centrifuged for 10 minutes at 1500 xg suspended in 25 ml of serum-free Dulbecco's modified Eagle's medium (DMEM-Gibco), recentrifuged for an additional 10 minutes at 1500 xg, resuspended in an additional 25 ml of DMEM and centrifuged again. The resultant pellet was suspended slowly in 40% polyethylene glycol 1540 (Baker) in DMEM. This mixture was incubated for 5 minutes at room temperature, diluted slowly with 25 ml of DMEM, and centrifuged for an additional 10 minutes. The resulting fusion mixture was resuspended in 25 ml of DMEM, recentrifuged and resuspended in DMEM containing 20% fetal calf serum (FCS-Flow Labs), pennicillin, streptomycin, and hypoxanthine, thymidine, and aminopterin (HAT).

The fusion mixture, after mixing with feeder spleen cells, was dispensed into ten 96 well microtiter plates. The plates were incubated at 370° C. in a humidified atmosphere containing 90% air, 10% $CO_2$. After 18 days, including 4 changes of medium, the medium from each well was assayed for the presence of mouse anti-human IgM using the following assay.

The wells of EIA plates were coated with 1 $\mu$g of human IgM (1 $\mu$g/ml in PBS) and incubated at 4° C. overnight. The wells were emptied and post-coated with 1% BSA in PBS by incubating at least 15 minutes at room temperature. The wells were then emptied and 100 μl of growth medium from each of the hybridoma cultures was added to the appropriate IgM-coated wells. These plates were incubated at 37° in a humidified atmosphere for 2 hours, the wells were emptied, washed twice with PBS, and then 100 μl of a 1:1000 (in PBS-BSA) dilution of (human IgM absorbed), peroxidase conjugated goat anti-mouse IgG was added to each well. The plates were incubated a further 2 hours at room temperature. After this incubation, the wells were washed five times with PBS and 100 μl of a 4 mg/ml orthophenylenediamine, 0.02% (v/v) hydrogen peroxide in sodium citrate, pH 4.5, solution was added. After 15 minutes, the reaction was stopped by adding 100 μl of 4N HC1 to each well. The presence of color in a well indicated the presence of mouse anti-human IgM in the corresponding well of the hybridoma plate. Of 656 hybridoma colonies (from the 960 wells), 14 colonies were secreting anti-human IgM, as determined by this screening procedure.

The invention may be embodied in other specific forms without departing from the spirit and scope thereof. Accordingly, other embodiments are within the following claims.

What is claimed is:

1. A process for inducing an immune response in an animal body, said process comprising the steps of:
   A. providing a living cell which secretes an antigen capable of inducing an immune response in said animal body;
   B. encapsulating said cell within a membrane comprising pores and defining an intracapsular volume with which said cell is suspended;
   C. controlling the dimensions of the pores to permit passage therethrough of said antigen but to preclude passage therethrough of said cell;
   D. implanting said encapsulated cell in said animal body;
   E. permitting said secreted antigen to traverse said membrane within said animal body to induce an immune response; and
   F. harvesting an antibody complementary to said antigen from the circulatory system of said animal body.

2. The process of claim 1 wherein said cell comprises a hybridoma cell.

3. The process of claim 2 comprising the additional steps of supplying nutrients to said cell and allowing said cells to undergo mitosis to produce a plurality of said cells.

4. The process of claim 3 wherein said supplying step is conducted prior to step B and wherein a plurality of said cells is encapsulated in step B.

5. The process of claim 3 wherein said supplying step is conducted after step B whereby a plurality of said cells is produced within said intracapsular volume.

6. The process of claim 3 wherein said supplying step is conducted after step D.

7. The process of claim 2 comprising the additional steps of:
   F. removing a lymphocyte which produces an antibody complementary to said antigen from said animal body;
   G. fusing said lymphocyte with an immortal cell line to form a hybridoma which produces said antibody; and
   H. culturing said hybridoma.

8. The process of claim 7 wherein said immortal cell line comprises a myeloma.

9. The process of claim 1 wherein said antigen has a molecular weight greater than 100,000 daltons.

10. The process of claim 1 wherein said cell additionally secretes an IgM and wherein the dimensions of said pores are controlled such that IgM is substantially retained within said intracapsular volume.

11. The process of claim 1 wherein said cell is a genetically modified cell.

12. The process of claim 1 comprising the additional steps of:
   F. harvesting said antibody by removing a lymphocyte which produces said antibody;
   G. fusing said lymphocyte with an immortal cell line to form a hybridoma which produces said antibody; and
   H. culturing said hybridoma.

13. The process of claim 12 wherein said immortal cell line comprises a myeloma.

14. The process of claim 1 wherein said cell is a prokaryotic cell.

15. The process of claim 14 wherein said prokaryotic cell secretes a pyrogen having a molecular weight greater than 70,000 daltons, said antigen has a molecular weight less than about 70,000 daltons, and during step C, the dimensions of said pores are controlled such that at least a portion of said pyrogen is retained within said intracapsular volume.

16. The process of claim 1 wherein said cell is a eukaryotic cell.

17. A process for producing monoclonal antibody complementary to an antigen secreted by a cell, said process comprising the steps of:
   A. encapsulating said cell within a membrane defining an intracapsular volume within which said cell is suspended, said membrane comprising pores having dimensions sufficient to permit passage therethrough of said antigen but to preclude passage therethrough of said cell;
   B. implanting said encapsulated cell in an animal body;
   C. permitting said secreted antigen to traverse said membrane within said animal body to induce a lymphocyte to produce antibody complementary to said secreted antigen;
   D. removing said lymphocyte from said animal body;
   E. fusing said lymphocyte with an immortal cell line to form a hybridoma which produces said antibody; and
   F. harvesting monoclonal antibody produced by said hybridoma.

18. The process of claim 17 wherein said immortal cell comprises a myeloma.

19. The process of claim 17 comprising the additional step of supplying nutrients to said cell and allowing said cell to undergo mitosis to produce a plurality of said cells.

20. The process of claim 19 wherein said supplying step is conducted prior to step A and wherein a plurality of said cells is encapsulated in step A.

21. The process of claim 19 wherein said supplying step is conducted after step B whereby a plurality of said cells is produced within said intracapsular volume.

22. The process of claim 17 wherein said encapsulated cell is implanted subcutaneously by injection.

23. The process of claim 17 wherein said cell comprises a genetically modified cell.

24. The process of claim 17 wherein said cell comprises a hybridoma cell.

25. The process of claim 17 wherein said cell comprises a eukaryotic cell.

26. The process of claim 17 wherein said cell comprises a prokaryotic cell.

27. The process of claim 17 wherein said antigen has a molecular weight greater than 100,000 daltons.

28. The process of claim 17 wherein said cell secretes a glycolipid, glycoprotein, lipoprotein, polysaccharide or protein having a molecular weight greater than about 400,000 daltons and said antigen has a molecular weight less than about 400,000 daltons, said process comprising the additional step of controlling the dimensions of the pores of said membrane during step A such that at least a portion of said glycolipid, glycoprotein, lipoprotein, polysaccharide or protein is retained within said intracapsular volume.

29. The process of claim 17 wherein said cell secretes a pyrogen having a molecular weight greater than 70,000 daltons and said antigen has a molecular weight less than about 70,000 daltons, said process comprising the additional step of controlling the dimensions of the pores of said membrane during step A such that at least a portion of said pyrogen is retained within said intracapsular volume.

30. The process of claim 17 wherein said membrane comprises pores of dimensions sufficient to permit tranverse of said antigen but to retain at least a portion of high molecular weight substances secreted by said cell.

* * * * *